United States Patent
Nakagawa et al.

(10) Patent No.: US 6,851,853 B2
(45) Date of Patent: Feb. 8, 2005

(54) X-RAY DEVICE

(75) Inventors: Akira Nakagawa, Kyoto (JP); Tatsuya Araki, Omihachiman (JP); Kimihiro Takahama, Ibaraki (JP); Hiroshi Miyata, Kyoto (JP); Mitsuhiro Hashimoto, Kyoto (JP); Toshiaki Nakamura, Nagaokakyo (JP); Takahiro Kamitake, Osaka (JP)

(73) Assignee: Shimadzu Corporation, Kyoto (JP)

( * ) Notice: Subject to any disclaimer, the term of this patent is extended or adjusted under 35 U.S.C. 154(b) by 128 days.

(21) Appl. No.: 10/394,143

(22) Filed: Mar. 24, 2003

(65) Prior Publication Data

US 2003/0190014 A1 Oct. 9, 2003

(30) Foreign Application Priority Data

Apr. 2, 2002 (JP) ........................................ 2002-099566

(51) Int. Cl.$^7$ ................................................. H05G 1/02

(52) U.S. Cl. ...................................... 378/197; 378/198

(58) Field of Search ................................ 378/193, 196, 378/197, 198

(56) References Cited

U.S. PATENT DOCUMENTS

| | | | | | |
|---|---|---|---|---|---|
| 3,790,805 | A | * | 2/1974 | Foderaro | 378/198 |
| 3,986,697 | A | * | 10/1976 | Amor et al. | 378/197 |
| 4,435,830 | A | * | 3/1984 | Suzuki et al. | 378/197 |
| 4,501,011 | A | * | 2/1985 | Hauck et al. | 378/196 |
| 4,875,228 | A | * | 10/1989 | Archer | 378/197 |
| 5,067,145 | A | * | 11/1991 | Siczek et al. | 378/198 |
| 5,475,730 | A | * | 12/1995 | Galando | 378/157 |
| 5,636,259 | A | * | 6/1997 | Khutoryansky et al. | 378/197 |
| 6,155,713 | A | * | 12/2000 | Watanabe | 378/197 |
| 6,496,558 | B2 | * | 12/2002 | Graumann | 378/39 |

* cited by examiner

*Primary Examiner*—Allen C. Ho
(74) *Attorney, Agent, or Firm*—Manabu Kanesaka

(57) ABSTRACT

An X-ray device includes a cart, a pole vertically provided on the cart, and a telescopic-type extendable supporting arm. The extendable supporting arm is formed of a hollow first arm with one end attached to the pole, a hollow second arm inserted in the first arm to be horizontally movable therein, and a third arm inserted in the second arm to be horizontally movable therein. Also, an X-ray tube device is provided on one end of the third arm. The extendable supporting arm has a synchronous moving mechanism for horizontally moving the third arm according to a horizontal movement of the second arm, and an extension/contraction operating handle attached to the second arm.

5 Claims, 4 Drawing Sheets

X-RAY DEVICE

BACKGROUND OF THE INVENTION AND RELATED ART STATEMENT

The invention relates to an X-ray device to be moved close to a bed and take an X-ray photograph in a sickroom or an operating room.

As shown in FIG. 3, an X-ray device 20 has a cart 23 provided with a pair of front wheels 21 and a pair of rear wheels 22 on both sides, and a pole 24 is rotatably disposed at a front portion of the cart. A supporting stand 25 movable vertically along the pole 24 is provided to the pole 24. A supporting arm 26 is extended horizontally from one end of the supporting stand. An X-ray tube device 28 with a collimator 27 is attached to a forward end of the supporting arm 26, so that the X-ray tube device can roll (rotate in the front and rear directions of the X-ray tube device) and pitch (rotate an arm shaft of the X-ray tube device) to adjust an X-ray irradiation direction. A control device 29 having an X-ray generating device including a transformer and the like is installed in a rear portion of the cart 23.

Also, a handle 30 is attached to a rear upper side of the control device 29, so that an operator can operate and steer the cart 23 while holding the handle 30.

Further, an operating handle 31 for adjusting the X-ray irradiation direction is attached to the collimator 27 disposed to the X-ray tube device 28. Incidentally, a reference numeral 32 is an operating switch of a locking mechanism (braking mechanism) of the supporting arm 26 attached to the operating handle 31.

When a doctor examines a patient, the X-ray device 20 is moved close to a bed where the patient is lying with a face up. After a film cassette is placed between the patient and the bed, the X-ray tube device 28 irradiates the X-ray on a part of the patient to take an X-ray photograph.

As described above, there is a case that, the X-ray device is moved close to the bed to take the X-ray photograph. In such a case, the X-ray tube device is supported on one end of an extendable supporting arm, called a telescopic arm. Therefore, when the X-ray device is moved or housed, the supporting arm is contracted to house the X-ray tube device. When the photograph is taken, the supporting arm is extended to an appropriate position. In order to position the X-ray tube device in a wider area and to make the device compact, as shown in the drawing, the extendable supporting arm 26 is normally formed of an outer arm 26a, an intermediate arm 26b horizontally moving in the outer arm 26a, and an inner arm 26c horizontally moving in the intermediate arm 26b. All of the three arms are formed in a cylindrical shape, that is, the three arms are directly connected in a telescopic manner to constitute a three stage extendable arm. One end of the outer arm 26a is fixed to the supporting stand 25 movable vertically along the pole 24, and one end of the inner arm 26c is attached to the X-ray tube device 28, thereby making it possible to roll and pitch.

Incidentally, in the drawing, a solid line shows a state that the extendable supporting arm 26 is contracted and positioned over the control device 29 to be housed. Likewise, a hidden line shows a state that the extendable supporting arm 26 is extended (projected) in front of the cart 23 after rotating the pole 24 by 180°.

In the conventional X-ray device wherein the X-ray tube device is supported by the three stage extendable supporting arm, there are the following problems.

Namely, when the doctor examines the patient and the X-ray photograph is taken, it is necessary to move the X-ray device 20 close to the bed. Then, the operating switch 32 is operated to release the lock while holding the operating handle 31 attached to the collimator 27. Then, the operator lifts or lowers the X-ray tube device 28, or moves the extendable supporting arm 26 to adjust the position of the X-ray tube device.

In a case that the bed is not located near a wall or a window, the operator can stand on a side opposite to the X-ray device 20 located close to the bed. Therefore, it is easy to move the X-ray tube device 28 vertically while operating the operating switch 32 with the operating handle 31, or adjust the position of the X-ray tube device 28 by extending or contracting the extendable supporting arm 26.

However, as shown in FIG. 4, in a case that the bed B is located close to the wall, it is difficult for the operator to walk around the side opposite to the X-ray device 20. Thus, as shown in the drawing, the operator has to extend an arm in a stretched posture to hold the operating handle attached to the collimator for the adjustment. Thus, it is difficult to operate and adjust the position of the X-ray tube device 28 accurately. Especially, the operator has to take the stretched posture when the extendable supporting arm 26 is extended.

Further, when a short operator takes the X-ray photograph, and a large space is needed between the X-ray tube device and the film, it is very difficult for the operator to adjust the position of the X-ray tube device. In this case, the operator may clime up on the bed B to hold the operating handle 31. However, although the stretched posture of the operator is avoided, the patient may receive bad influence depending on a condition of the patient. Also, the bed B may deform, thereby preventing accurate positioning.

In view of the above problems, the present invention has been made and an object of the invention is to provide an X-ray device, wherein even if the bed is located close to a wall or window, the operator can adjust the position of the X-ray tube device in a comfortable posture. Especially, the operator can extend the extendable supporting arm in the comfortable posture.

Further objects and advantages of the invention will be apparent from the following description of the invention.

SUMMARY OF THE INVENTION

To attain the above objects, according to the present invention, an X-ray device includes a cart, a pole vertically provided on the cart, and a telescopic-type extendable supporting arm. The extendable supporting arm is formed of a cylindrical first arm with one end attached to the pole, a cylindrical second arm inserted in the first arm to be horizontally movable therein, and a cylindrical third arm inserted in the second arm to be horizontally movable therein. Also, the X-ray device includes an X-ray tube device provided on one end of the third arm. The extendable supporting arm has a synchronous moving mechanism for horizontally moving the third arm according to a horizontal movement of the second arm, and an extension/contraction operating handle attached to the second arm.

The synchronous moving mechanism is a mechanism for moving the third arm in the same direction as that the second arm moves. That is, when the second arm moves in a direction pushed (contracted) into the first arm, the synchronous moving mechanism moves the third arm in a direction pushed (contracted) into the second arm. When the second arm moves in a direction withdrawn (extended) from the first arm, the synchronous moving mechanism moves the third arm in a direction withdrawn (extended) from the second arm. Also, in a case that the second arm moves in the first arm by a moving distance D1 and the third arm moves in the second arm by a moving distance D2, it is acceptable that either D1 equals to D2 or D1 does not equal to D2.

Also, it is preferable that the synchronous moving mechanism is formed of a pair of sprockets disposed in the second arm and a chain wound around the pair of the sprockets. Also, it is preferable that the first arm is connected to one end of the chain wound around the pair of the sprockets, and the third arm is connected to the other end thereof.

Incidentally, the chain may be a timing belt, and the chain in the second aspect of the invention includes the timing belt.

Further, it is preferable to include a locking mechanism for locking the second arm in the first arm. It is also preferable that an operating device, such as a switch, of the locking mechanism is provided to the extension/contraction operating handle attached to the second arm.

According to the structure as described above, the one end of the chain wound around the pair of the sprockets is fixed or connected to the first arm. Therefore, when the second arm is moved horizontally while holding the extension/contraction operating handle attached to the second arm, the third arm is also moved in the same direction as that of the second arm by the same moving quantity. Also, since the operation device of the locking mechanism is attached to the extension/contraction operating handle, the operator can adjust the position of the X-ray tube device in a comfortable posture.

DETAILED DESCRIPTION OF PREFERRED EMBODIMENTS

Hereunder, embodiments of the present invention will be explained with reference to the accompanying drawings.

FIGS. 1(*a*)–1(*d*) are schematic views showing a structure of a telescopic-type three stage extendable supporting arm formed of the first arm, the second arm and the third arm constituting an essential part of the present invention. One end of the three stage extendable supporting arm is attached to a pole rotatably disposed to a cart, as in this type of a conventional device, to horizontally support an X-ray tube device having a collimator.

Figure 3:
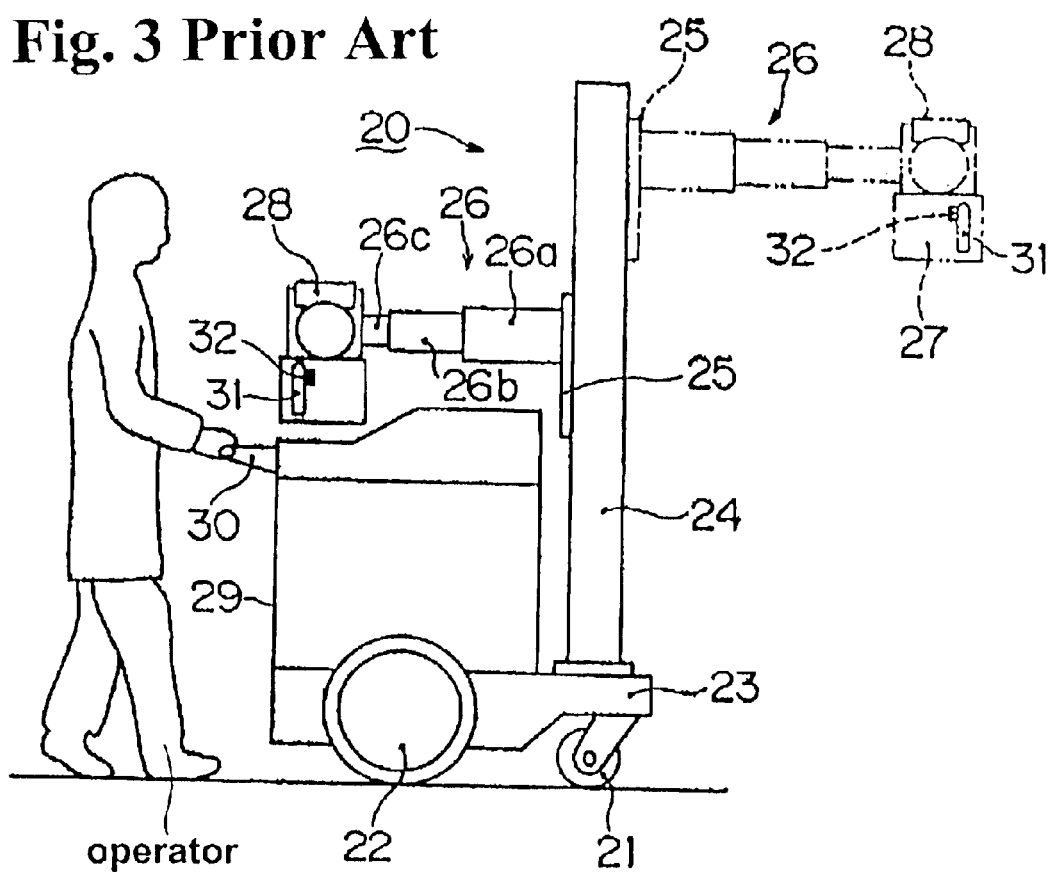
FIG. 3 is a diagram showing a conventional X-ray device.

FIG. 1(*a*) is a side sectional view; FIG. 1(*b*) is a sectional view taken along line 1(*b*)—1(*b*) in FIG. 1(*a*); FIG. 1(*c*) is a plan sectional view showing an extended state of the three stage extendable supporting arm; and FIG. 1(*d*) is a plan sectional view showing a contracted state of the three stage extendable supporting arm. The constituting elements having the same functions as those in FIG. 3 are designated with the same symbols used in FIG. 3, and explanations thereof are omitted.

As shown in the drawings, the extendable supporting arm 1 includes the first arm 2, the second arm 3 and the third arm 4 formed of a hollow (square hollow in the present embodiment) member. Each of the first arm 2 and the second arm 3 has a pair of rails 5, 6 on an inner peripheral surface facing each other in an axial direction. The second arm 3 and the third arm 4 are provided with supporting bearings or rollers 7, 8 for holding the rails 5, 6. The second arm 3 engages the rails 5 provided in the first arm 2 to be movable in a horizontal direction through the supporting bearings 7. The third arm 4 engages the rails 6 provided in the second arm 3 to be movable in a horizontal direction through the supporting bearings 8.

Incidentally, one end (right end in the drawing) of the first arm 2 is fixed to a supporting member, which is attached to a pole rotatably provided in a cart (not shown) and movable in a vertical direction.

A pair of sprockets 9, 10 is provided inside a square hollow member of the second arm 3 with a space therebetween in the axial direction thereof. A chain 11 extends around the sprockets 9, 10, and one end of the chain 11 is connected or fixed to the first arm 2 through a fixture 12 made of a metal or the like, and the other end thereof is connected or fixed to the third arm 4 through a fixture 13 made of a metal or the like. Also, on an upper portion of the distal end of the second arm 3 at a side of the X-ray tube device 28, an extension/contraction operating handle 14 is provided for horizontally moving (extending or contracting) the second arm 3 with respect to the first arm.

An electromagnetic brake 15 is provided in the first arm 2 as a locking mechanism for locking the second arm 3 in the first arm 2. The electromagnetic brake 15 is preferable to be a dead-man type (a brake that can be released when a handle is grasped) for safety. A releasing switch (operating device of the locking mechanism) 16 thereof is provided in the extension/contraction operating handle 14.

Next, the extension/contraction movement of the telescopic-type three stage extendable supporting arm 1 having the above structure will be explained.

In FIG. 1(*c*) showing a state wherein the three stage extendable supporting arm 1 is extended, when an operator holds the extension/contraction operating handle 14, the lock releasing switch 16 is operated to release the electromagnetic brake from locking the second arm 3 with respect to the first arm 2.

Under this state, when the second arm 3 moves in an arrow a direction (right direction in the drawing) to be inserted into the first arm 2, since one end of the chain 11 wound around the sprockets 9, 10 is fixed to the first arm 2 through the fixture 12, the other end of the chain 11 is rotated in an arrow b direction as the second arm 3 moves in the arrow a direction. Since the third arm 4 is connected to the other end of the chain 11 through the fixture 13, the third arm 4 enters the second arm 3 by the same length as a length (moved length) that the second arm 3 enters the first arm 2, thereby being contracted. The most contracted state is shown in FIG. 1(*d*).

Also, from the state as shown in FIG. 1(*d*), when the second arm 3 moves away from the first arm 2 in the withdrawing direction (in the direction opposite to the arrow a in FIG. 1(*c*)) while holding the extension/contraction operating handle 14, the chain 11 wound around the sprockets 9, 10 is rotated in the direction opposite to the arrow b as shown in FIG. 1(*c*), so that the third arm 4 is withdrawn from the second arm 3 to be extended by the same length as the withdrawn length (moved length) of the second arm 3 from the first arm 2. The most extended state is shown in FIG. 1(*c*).

Figure 1A:
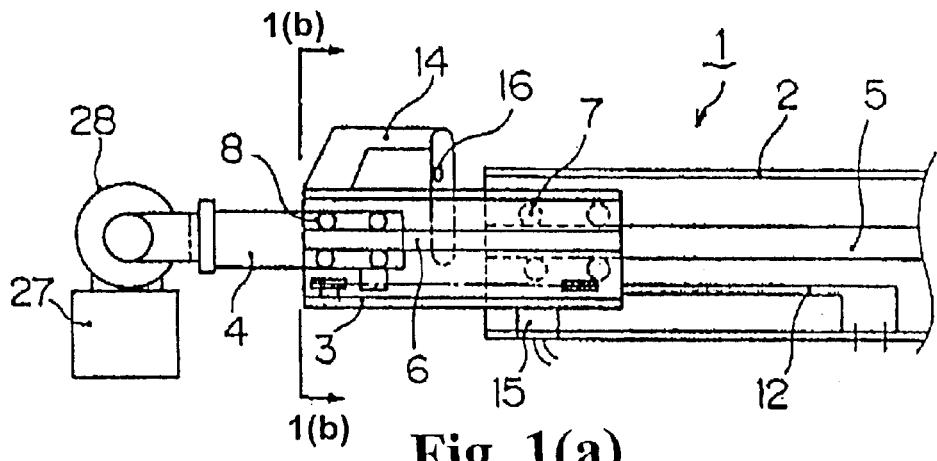
FIG. 1(*a*) to FIG. 1(*d*) are schematic sectional views showing a structure of an essential portion of the present invention.
Figure 1C:
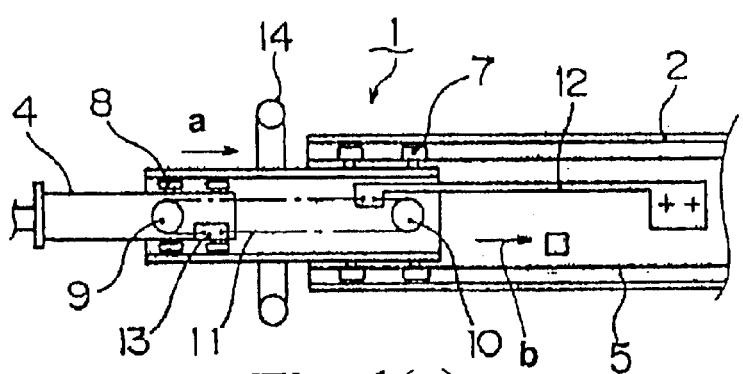
Figure 1D:
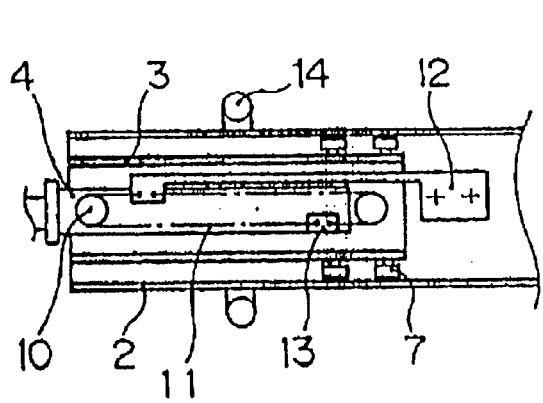
Figure 1B:
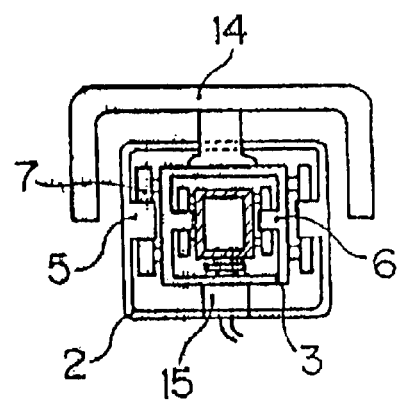
Figure 2:
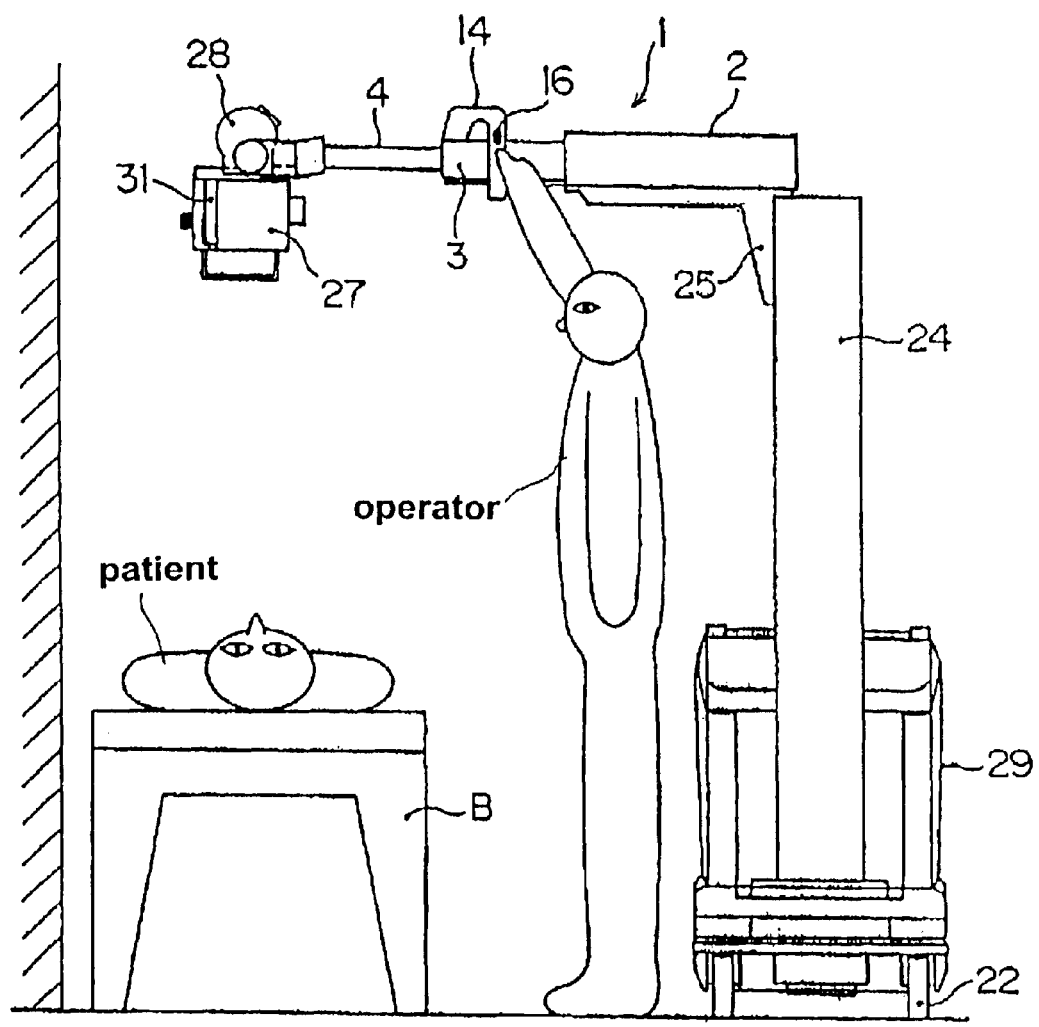
FIG. 2 is a diagram showing an operational state of an X-ray device of the present invention.
Figure 4:
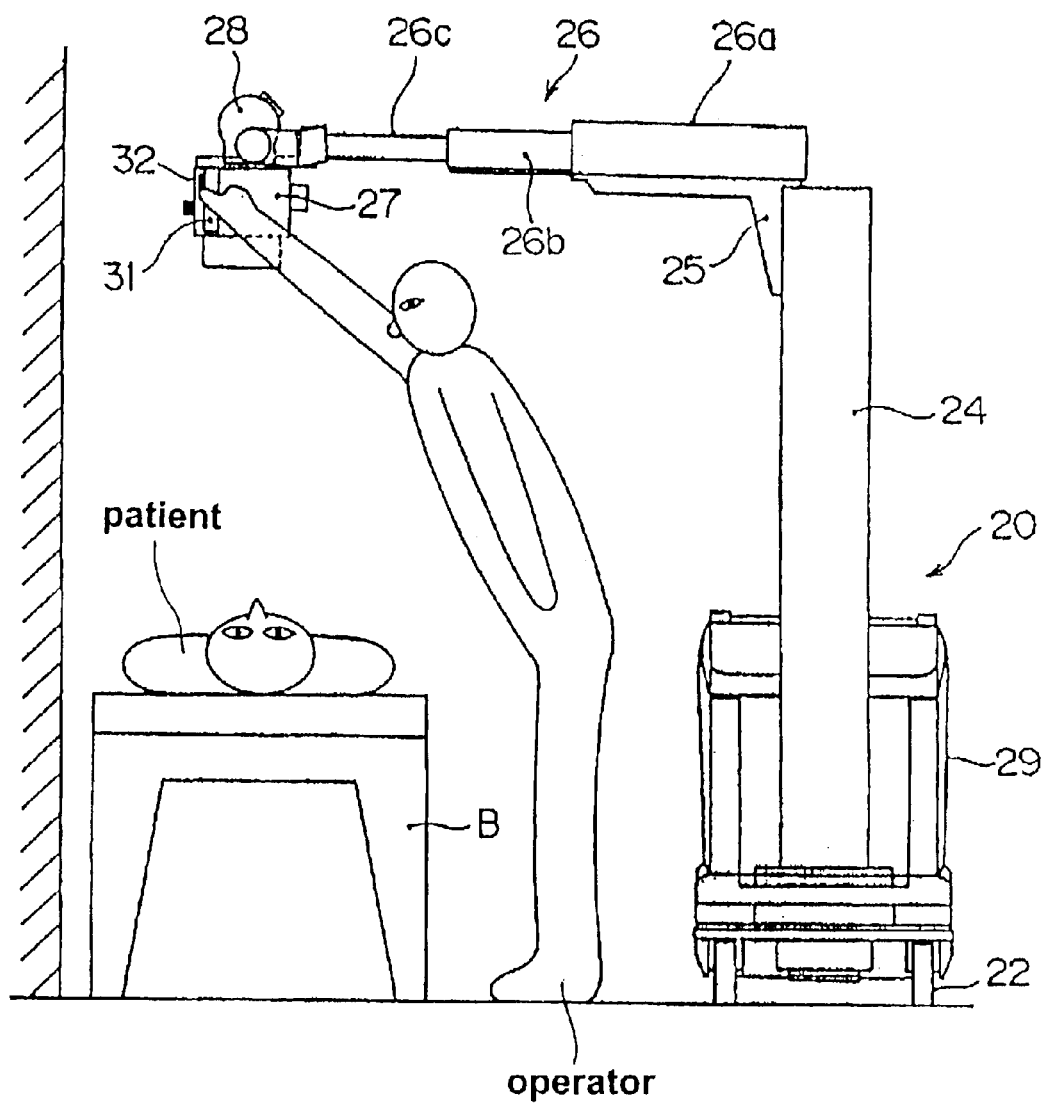
FIG. 4 is a diagram showing an operational state of the conventional X-ray device shown in FIG. 3.

FIG. 2 shows an operational state of the X-ray device wherein the telescopic-type three stage extendable supporting arm 1 having a structure shown in FIGS. 1(a) to 1(d) supports an X-ray tube device at one end thereof. According to this device, even if a bed B is positioned close to a wall, since the extendable supporting arm 1 can be operated with the extension/contraction operating handle 14 provided in the second arm 3, the operator can easily extend or contract the extendable supporting arm 1 in a comfortable posture. Therefore, the X-ray tube device 28 attached to the end of the third arm 4 can be accurately positioned to thereby improve the operating ability. Incidentally, in FIG. 2, reference numerals 22, 24, 25 are the same constitutional elements as in FIGS. 3 and 4.

In the above-described embodiment, the synchronous movement mechanism is formed of the pair of the sprockets and the chain. However, for example, it is also possible that a synchronous movement mechanism is configured such that the second arm and the third arm may be provided with racks, respectively, and a pair of pinions engaging both racks may be provided to the second arm.

As described above, in a case that the synchronous movement mechanism is formed of the racks and pinions, it is possible to change a ratio of the tooth numbers of the two pinions engaging the racks to make an extended/contracted length of the second arm with respect to the first arm (length to be inserted/length to be withdrawn) different from an extended/contracted length of the third arm with respect to the second arm (length to be inserted/length to be withdrawn).

However, in the case that the synchronous movement mechanism is formed of the pair of the sprockets and the chain, as in the above embodiment, the structure becomes simpler and the extendable supporting arm can be made light and compact to thereby make the device light and compact.

According to the X-ray device of the present invention, as described above, the extension/contraction operation of the three stage extendable arm for supporting the X-ray tube device can be carried out by the extension/contraction operation of the intermediate arm.

As a result, even if a bed is positioned close to a wall, an operator can position the X-ray tube device in a comfortable posture, so that the X-ray device has the improved operating ability.

While the invention has been explained with reference to the specific embodiments of the invention, the explanation is illustrative and the invention is limited only by the appended claims.

What is claimed is:

1. An X-ray device comprising:

a supporting base member having a pole, an X-ray tube device for taking an X-ray photograph, and an extendable supporting arm including a hollow first arm extending from the pole, a hollow second arm inserted in the first arm to be movable therein, a third arm inserted in the second arm to be movable in the second arm and having a distal end attached to the X-ray tube device, a synchronous moving mechanism disposed in the extendable supporting arm for moving the third arm in the second arm when the second arm moves in the first arm, and an operating handle attached to the second arm for moving the second arm.

2. An X-ray device according to claim 1, wherein said synchronous moving mechanism includes a pair of sprockets disposed in the second arm and a chain wound around the pair of the sprockets, said chain having one end connected to the first arm and the other end connected to the third arm.

3. An X-ray device according to claim 1, wherein said synchronous moving mechanism includes a pair of rotation members disposed in the second arm and an endless member wound around the pair of the rotation members, said endless member having one end connected to the first arm and the other end connected to the third arm.

4. An X-ray device according to claim 1, further comprising a locking mechanism disposed in the extendable supporting arm for locking the second arm, and an operating device provided at the operating handle for operating the locking mechanism.

5. An X-ray device according to claim 1, wherein said supporting base member is a portable cart, and said locking mechanism is an electromagnetic brake.

* * * * *